(12) United States Patent
Radl et al.

(10) Patent No.: US 11,389,318 B2
(45) Date of Patent: Jul. 19, 2022

(54) SYSTEM INCLUDING SUCTION REGULATOR FOR AUTOMATICALLY REMOVING URINE FROM A FEMALE PATIENT

(71) Applicant: Boehringer Technologies, LP, Phoenixville, PA (US)

(72) Inventors: Christopher L. Radl, Malvern, PA (US); Michael Reed Vennel, Phoenixville, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 128 days.

(21) Appl. No.: 16/833,980

(22) Filed: Mar. 30, 2020

(65) Prior Publication Data

US 2020/0315836 A1 Oct. 8, 2020

Related U.S. Application Data

(60) Provisional application No. 62/872,397, filed on Jul. 10, 2019, provisional application No. 62/829,731, filed on Apr. 5, 2019.

(51) Int. Cl.
*A61F 5/44* (2006.01)
*A61F 5/455* (2006.01)
*A61M 1/00* (2006.01)

(52) U.S. Cl.
CPC ............ *A61F 5/4405* (2013.01); *A61F 5/455* (2013.01); *A61M 1/74* (2021.05); *A61M 2202/0496* (2013.01); *A61M 2205/3334* (2013.01); *A61M 2205/702* (2013.01); *A61M 2210/14* (2013.01)

(58) Field of Classification Search
CPC ......... A61F 5/4405; A61F 5/455; A61M 1/74; A61M 2205/702; A61M 2202/0496; A61M 2205/3334; A61M 2210/14
See application file for complete search history.

(56) References Cited

U.S. PATENT DOCUMENTS

| 4,610,675 A | 9/1986 | Triunfol |
| 4,631,061 A | 12/1986 | Martin |
| 4,747,166 A | 5/1988 | Kuntz |

(Continued)

OTHER PUBLICATIONS https://www.crbard.com/Medical/en-US/Products/PUREWICK-Female-External-Catheter, undated, 1 page.

(Continued)

*Primary Examiner* — Tatyana Zalukaeva
*Assistant Examiner* — Nhu Q. Tran
(74) *Attorney, Agent, or Firm* — Caesar Rivise, PC

(57) ABSTRACT

A system for automatically removing by suction urine voided by a female. The system includes an external catheter, a canister and a suction regulator. The external catheter is applied at the urethra opening to receive urine voided by the female. The canister collects the urine and is coupled to a source of suction having a first value. The suction regulator is interposed between the external catheter and the canister to regulate the amount of suction to a regulated value which is applied the external catheter, whereupon urine from the external catheter is carried through the suction regulator and into the canister. The system may also include an adapter or an adapter/splitter for connection between the source of suction and the canister.

10 Claims, 9 Drawing Sheets

(56) References Cited

U.S. PATENT DOCUMENTS

| | | | |
|---|---|---|---|
| 5,466,229 A | 11/1995 | Elson et al. | |
| 5,678,564 A | 10/1997 | Lawrence et al. | |
| 5,894,608 A | 4/1999 | Birbara | |
| 6,024,120 A * | 2/2000 | Yam | F16K 24/06 137/495 |
| 6,849,065 B2 | 2/2005 | Schmidt et al. | |
| 7,018,366 B2 | 3/2006 | Easter | |
| 7,220,250 B2 | 5/2007 | Suzuki et al. | |
| 8,287,508 B1 | 10/2012 | Sanchez | |
| 10,646,625 B2 | 5/2020 | Radl et al. | |
| 2002/0087131 A1 | 7/2002 | Wolff et al. | |
| 2004/0182393 A1* | 9/2004 | MacMillan | F16K 3/246 128/205.19 |
| 2005/0192548 A1* | 9/2005 | Dolliver | A61M 1/3698 604/317 |
| 2008/0015504 A1* | 1/2008 | Boehringer | A61M 1/74 604/119 |
| 2011/0282326 A1* | 11/2011 | Krupa | A61M 1/743 604/540 |
| 2012/0238972 A1* | 9/2012 | Karpowicz | A61M 1/74 604/319 |
| 2015/0088068 A1 | 3/2015 | Moulden et al. | |
| 2015/0359660 A1 | 12/2015 | Harvie | |
| 2017/0045149 A1* | 2/2017 | Hielkema | G05D 16/0655 |
| 2017/0266031 A1* | 9/2017 | Sanchez | A61F 5/4404 |

OTHER PUBLICATIONS https://www.ohmedical.com/External-Catheters/DRYDOCtrade-VACUUM-STATION-DD15/, 2020, 2 pages.
https://sageproducts.com/primafit-external-urine-management-system-for-females/, 2020, 3 pages.
International Search Report for PCT/US2020/026123 dated Jul. 21, 2020.

* cited by examiner

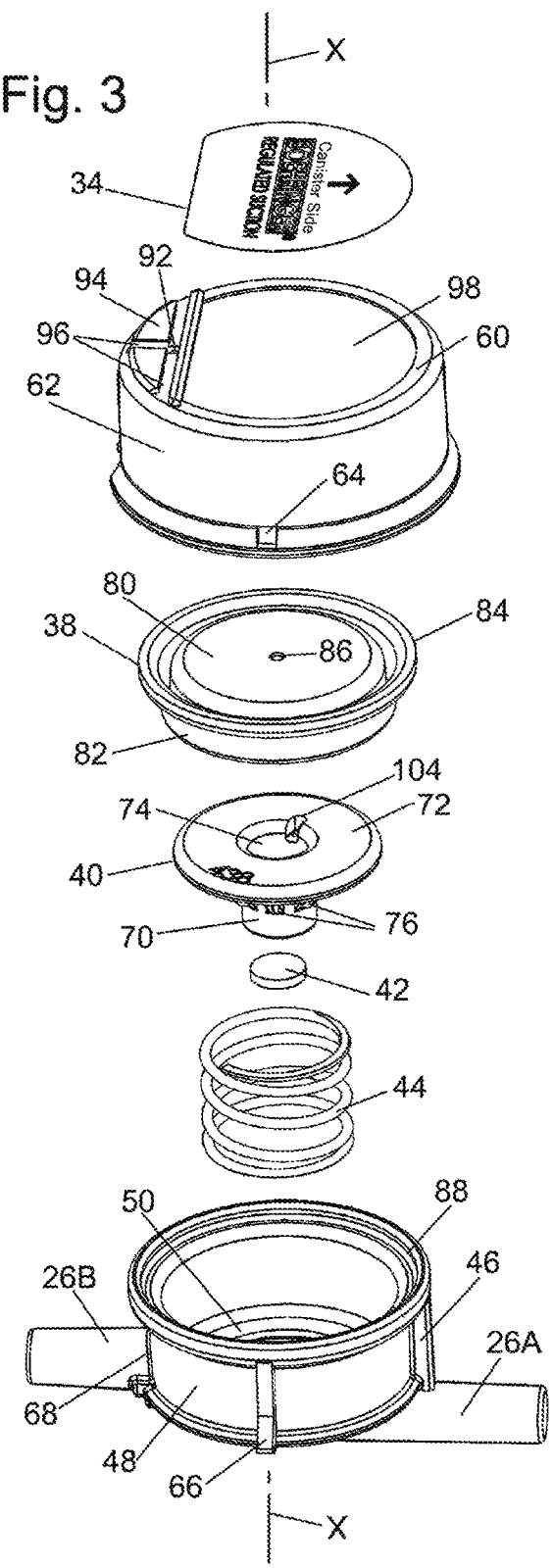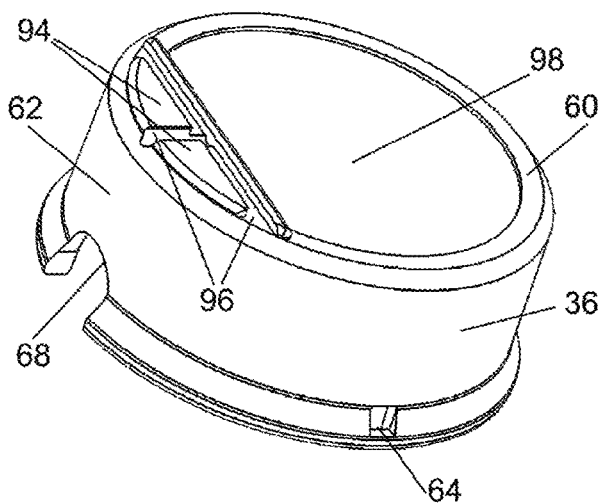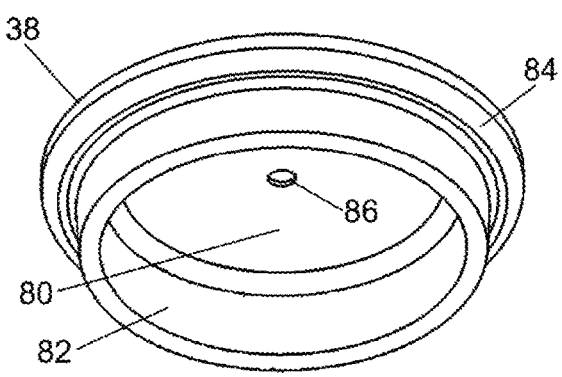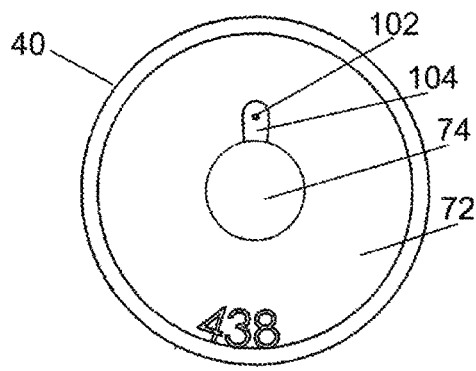

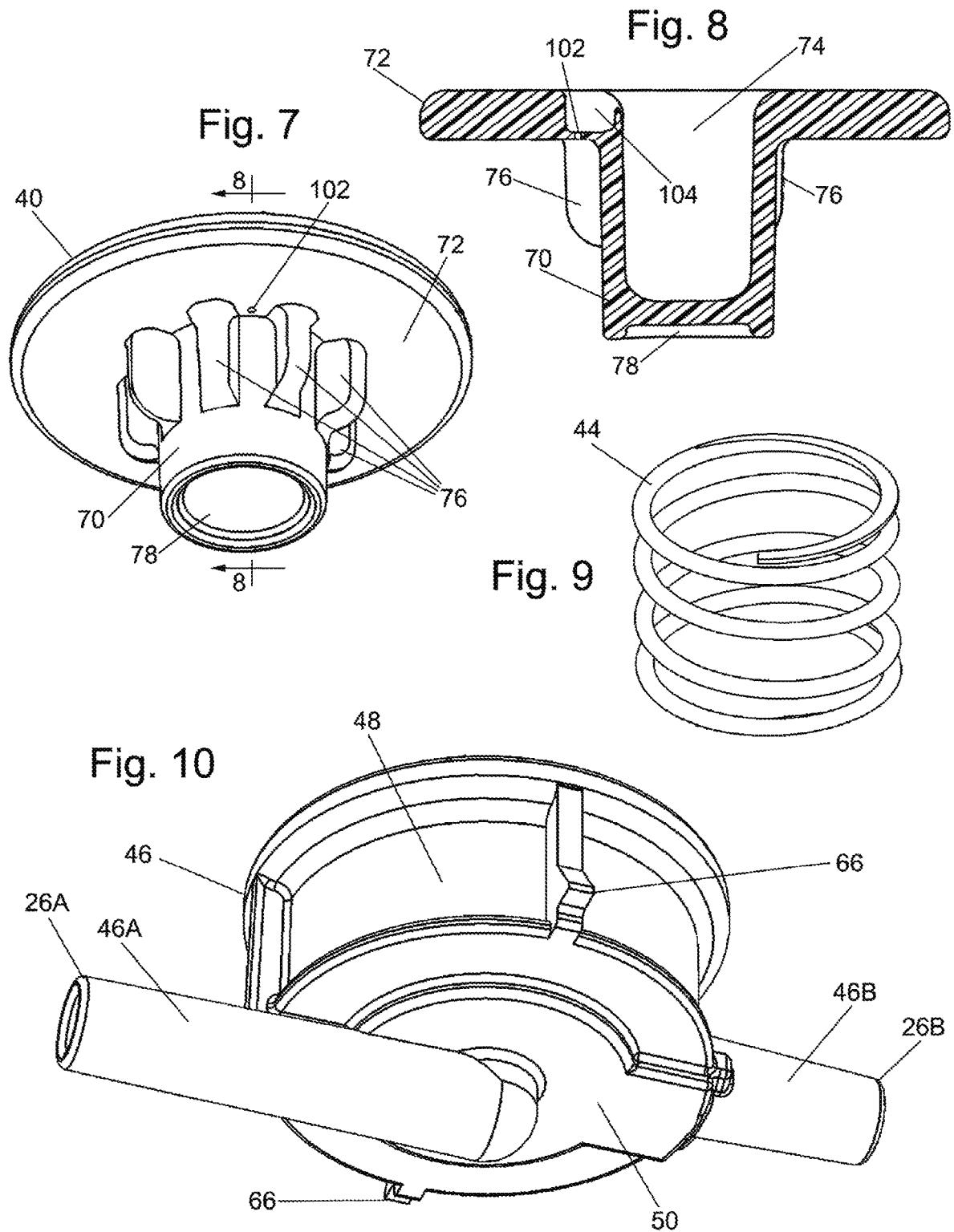

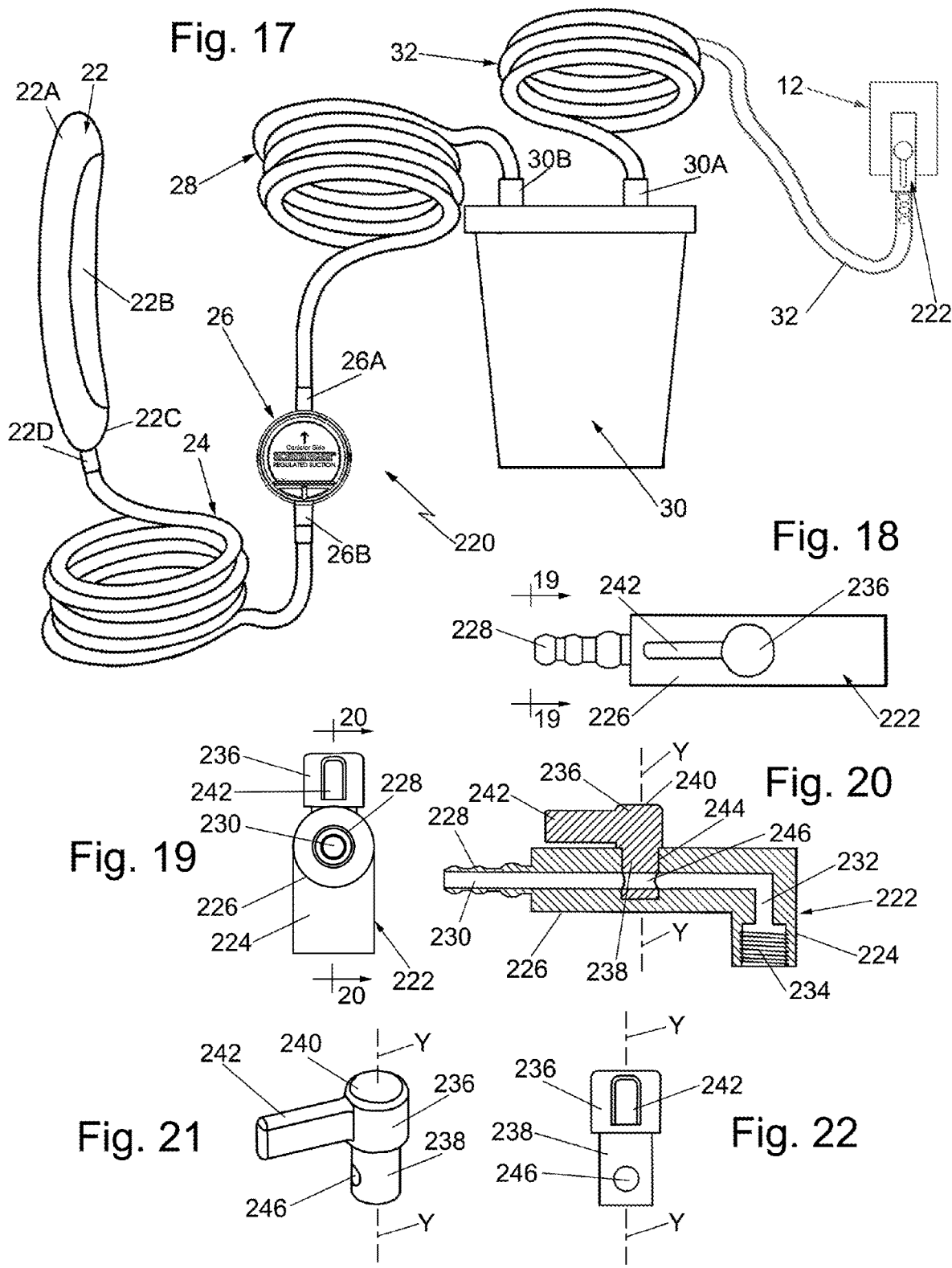

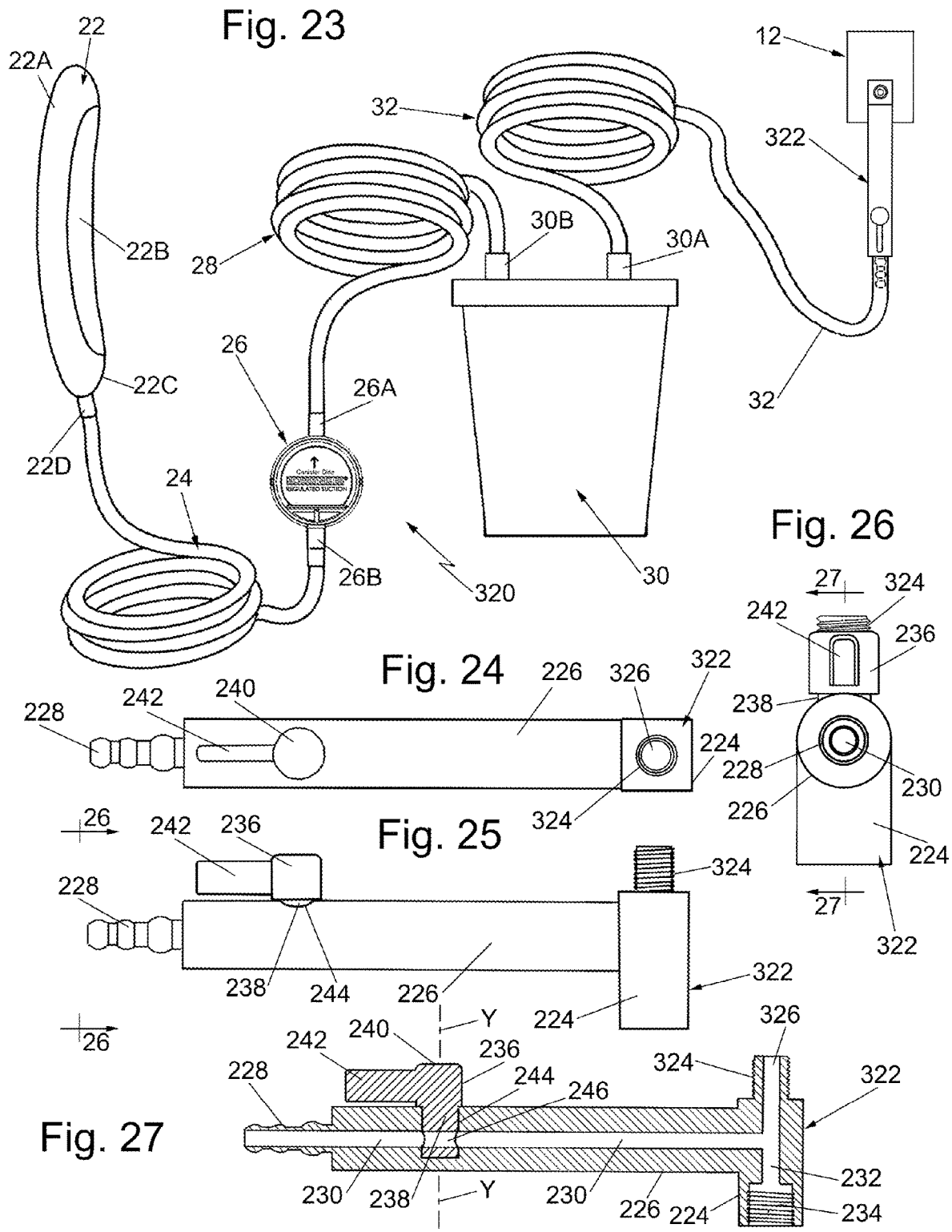

SYSTEM INCLUDING SUCTION REGULATOR FOR AUTOMATICALLY REMOVING URINE FROM A FEMALE PATIENT

CROSS-REFERENCE TO RELATED APPLICATIONS

This utility application claims the benefit under 35 U.S.C. § 119(e) of Provisional Application Ser. No. 62/829,731, filed on Apr. 5, 2019, entitled System Including Suction Regulator For Automatically Removing Urine From A Female Patient And Method Of Use Of The System, and Provisional Application Ser. No. 62/872,397 filed on Jul. 10, 2019, entitled System Including Sound Suppressed Suction Regulator For Automatically Removing Urine From A Female Patient Via An External Catheter And Method Of Removing Urine From A Female Patient Using An External Catheter. The entire disclosures of those two provisional applications are incorporated by reference herein.

FIELD OF THE INVENTION

This invention relates generally to medical devices and methods and more particularly to devices and methods for automatically removing urine from a female patient using suction applied to an external catheter.

BACKGROUND OF THE INVENTION

Various external catheters are available for non-invasive urine output management in female patients. The PUREWICK® female external catheter available from C.R. Bard, Inc. is an example of one such device. That external catheter is a soft member having a hollow flexible body including a side opening exposing soft absorbent gauze. The catheter is configured to be positioned so that soft gauze is disposed between the patient's separated gluteus and labia and in fluid communication with the urethral opening of the patient, whereupon urine voided by the patient is wicked into the gauze. The catheter is arranged to be attached via suction tubing to a suction canister, which should in turn be connected to either a suction regulator on a hospital wall or a portable suction pump, such as the DRYDOC™ vacuum suction station of C.R. Bard, Inc., whereupon the urine wicked into the external catheter is carried by the suction into the canister for collection. The Instructions for Use (IFU) of the PUREWICK® female external catheter indicates that the suction source should be set to a minimum of 40 mmHg continuous suction.

Sage Products, LLC, now a Stryker Corporation company, provides an external urine management system for females under the trademark PRIMAFIT. That system is in many respects similar to the PUREWICK® system. In particular, the PRIMAFIT system basically comprises an external catheter body having an end cap to fit in the woman's perineal area to secure the catheter in place. The catheter includes soft wicking fabric that absorbs and diverts urine away from the patient's skin. Urine is then absorbed into the system's core and suctioned into a collection canister.

The patented literature includes various systems and methods for collecting and transporting urine away from a person's body, such as: U.S. Pat. No. 4,610,675 (Triunfol); U.S. Pat. No. 4,747,166 (Kuntz); U.S. Pat. No. 5,678,564 (Lawrence et al.); U.S. Pat. No. 5,894,608 (Birbara); U.S. Pat. No. 6,849,065 (Schmidt et al.); U.S. Pat. No. 7,018,366 (Easter); U.S. Pat. No. 7,220,250 (Suzuki et al.); and U.S. Pat. No. 8,287,508 (Sanchez).

All of the references as cited herein are specifically incorporated by reference As will be appreciated by those skilled in the art, most hospital suction regulators provide insufficient flow at low vacuum pressures, like the 40 mmHg recommended for use with the PUREWICK® female external catheter. Therefore nurses or other care givers frequently increase the vacuum to get adequate urine flow. However, the use of higher vacuum pressure poses an increased risk to the patient, as the only opening in the circuit for air to relieve the pressure is adjacent the patient's genitalia. Accordingly, use of increased vacuum pressure to increase the flow rate of urine being withdrawn into the canister runs the risk of injury to the delicate issue adjacent the urethral opening.

Thus, a need exists for a system and method which is efficient for removing urine from a patient using an external catheter, wherein the flow rate is sufficiently high for increased effectiveness, yet is produced by a suction level that is sufficiently low to minimize the danger of injury to the delicate tissue of the patient adjacent the patient's urethral opening. The subject system addresses that need by providing a disposable suction regulator configured for use between the female external catheter and a canister coupled to a source of higher suction, e.g., a regulator at the hospital's suction line. To that end the disposable female external catheter suction regulator of this invention is designed in such a way that it allows far greater flow at low pressures than do the traditional wall regulators. As such, it is intended to be placed in the same circuit, but between the external catheter and the canister.

SUMMARY OF THE INVENTION

One aspect of this invention is a system for automatically removing by suction urine voided by a female. The system comprises an external catheter, a receptacle or canister, and a suction regulator. The external catheter is configured for external disposition in fluid communication with a urethra opening of the female, whereupon urine voided by the female is received by the external catheter. The receptacle or canister is configured for collecting urine and also configured to be coupled to a source of suction providing suction having a first value. The suction regulator is interposed between the external catheter and the receptacle to regulate the amount of suction from the first value to a regulated value lower than the first value and to apply regulated suction at the regulated value to the external catheter, whereupon urine from the external catheter is carried through the suction regulator and into the receptacle or canister.

In accordance with one preferred aspect of the system of this invention the receptacle or canister comprises a first port, a second port, and a hollow interior in fluid communication with the first and second ports. The first port is configured to be connected to the source of suction. The suction regulator comprises a first port and a second port. The second port of the suction regulator is configured for coupling to the second port of the receptacle or canister. The suction regulator is configured for providing the regulated suction at the first port thereof. The first port of the suction regulator is configured to be coupled to the external catheter to carry urine from the external catheter by the regulated suction through the suction regulator and into the first port of the receptacle or canister for collection in the hollow interior.

In accordance with another preferred aspect of the system of this invention the regulated value of suction is within the range of approximately 40-175 mmHg.

In accordance with another preferred aspect of the system of this invention the urine is carried through the suction regulator into the receptacle by air which is flowing at a flow rate up to approximately 100 standard cubic feet per hour (SCFH) (which converts to 47 liters per minute (LPM)).

In accordance with another preferred aspect of the system of this invention the regulator is disposable.

In accordance with another preferred aspect of the system of this invention the suction regulator comprises a first chamber, a second chamber, a movable diaphragm and a biasing member. The first chamber is configured to have suction applied thereto from the receptacle or canister. The second chamber is at atmospheric pressure. The movable diaphragm separates the first chamber from the second chamber, whereupon a differential pressure exists between the first and second chambers. The differential pressure imparts a differential pressure force on the movable diaphragm. The biasing member is configured to impart a counter force on the movable diaphragm that opposes the differential pressure force.

In accordance with another preferred aspect of the system of this invention the first chamber comprises a valve seat and a movable sealing member coupled to the movable diaphragm. The valve seat surrounds an opening for fluid within the first chamber to flow therethrough. The sealing member blocks the opening when the differential pressure force exceeds the counter force imparted by the biasing member.

In accordance with another preferred aspect of the system of this invention the suction regulator is configured to prevent the movable sealing member from becoming stuck on the valve seat.

In accordance with another preferred aspect of the system of this invention the suction regulator comprises a bleed hole in the diaphragm to enable ambient air from the second chamber to enter into the first chamber.

In accordance with another preferred aspect of the system of this invention the first and second chambers are located within a housing, and wherein the second chamber includes a bleed hole in the housing in communication with the ambient atmosphere.

In accordance with another preferred aspect of the system of this invention the bleed hole in the housing is located within a recess having at least one opening at an end thereof to prevent blockage of the bleed hole.

In accordance with another preferred aspect of the system of this invention the movable diaphragm has a natural shape, is molded from a flexible material, and does not require eversion for disposition in the suction regulator to separate the first chamber from the second chamber, whereupon the movable diaphragm is less prone to creep over time.

In accordance with another preferred aspect of the system of this invention urine is carried through the suction regulator and into the receptacle or canister by air and wherein the suction regulator comprises a body and a sound suppressor. The body has a first passageway configured to be coupled to the external catheter, a second passageway configured to be coupled to the source of suction, and third passageway connecting the first and second passageways to result in a tortuous fluid flow path through the passageways. The sound suppressor is located in the second passageway for reducing the sound of air flowing through the suction regulator.

In accordance with another preferred aspect of the system of this invention the second passageway is offset from the first passageway and interconnected thereto by a third passageway extending generally perpendicularly to the first and second passageways.

In accordance with another preferred aspect of the system of this invention the sound suppressor comprises a tube having a multitude of small hook-like projections extending generally radially inward.

In accordance with another preferred aspect of the system of this invention the system additionally comprises an adapter configured to be coupled between the source of suction and the receptacle or canister. The adapter comprises an inlet, a valve and a first connector. The inlet is configured to be connected to the source of suction. The first connector is configured to be connected to the receptacle or canister. The valve is configured to be in either a closed state or an open state, whereupon when in the closed state the receptacle or canister is isolated from the inlet, and when in the open state suction at the first value is provided from the inlet to the first connector and to receptacle or canister.

In accordance with another preferred aspect of the system of this invention the adapter includes an internal passageway having one end in communication with the inlet and another end in communication with the first connector, and wherein the valve includes a rotatable portion having an opening extending therethrough. The rotatable portion intersects the internal passageway, whereupon when the rotatable portion is in a first rotatable position the rotatable portion blocks the internal passageway between the inlet and the first connector, and when the rotatable portion is in a second position the opening unblocks the internal passageway between the inlet and the first connector to enable suction at the first value to appear at the first connector.

In accordance with another preferred aspect of the system of this invention the first connector is configured to have a first section of suction tubing having a first end connected to it and a second end connected to the receptacle or canister.

In accordance with another preferred aspect of the system of this invention the first connector is a barbed bubble connector.

In accordance with another preferred aspect of the system of this invention the adapter additionally comprises a splitter including a second connector having a passageway section in fluid communication with the internal passageway between the inlet and the valve, whereupon suction at the first value is available from the inlet to the second connector irrespective of the state of the valve.

In accordance with another preferred aspect of the system of this invention the adapter and splitter includes an internal passageway having one end in communication with the inlet and another end in communication with the first connector, and wherein the valve includes a rotatable portion having an opening extending therethrough. The rotatable portion intersects the internal passageway, whereupon when the rotatable portion is in a first rotatable position the rotatable portion blocks the internal passageway between the inlet and the first connector, and when the rotatable portion is in a second position the opening unblocks the internal passageway between the inlet and the first connector to enable suction at the first value to appear at the first connector.

In accordance with another preferred aspect of the system of this invention the urine is carried through the suction regulator into the receptacle by air flow, wherein a differential pressure between the external catheter and the suction regulator results, and wherein the system is configured so that the differential pressure of no more than approximately 55 mmHg provides an air flow rate of greater than 25 LPM.

In accordance with another preferred aspect of the system of this invention the urine is carried through the suction regulator into the receptacle by air flow, wherein a differential pressure between the external catheter and the suction regulator results, and wherein the system is configured so that the differential pressure of no more than approximately 100 mmHg provides an air flow rate of greater than 35 LPM.

In accordance with another preferred aspect of the system of this invention the urine is carried through the suction regulator into the receptacle by air flow and wherein the rate of the air flow is greater than 45 LPM.

In accordance with another preferred aspect of the system of this invention the urine is carried through the suction regulator into the receptacle by air flow and wherein the system exhibits a ratio the air flow rate in LPM squared to the regulated value is at least 13.

DESCRIPTION OF THE DRAWING

FIG. 3 is an exploded isometric view of the components making up the suction regulator shown in FIG. 2;

FIG. 4 is an enlarged isometric view of one of the components, i.e., a cap or lid, of the suction regulator shown in FIG. 2;

FIG. 5 is an enlarged isometric view of another of the components, i.e., a diaphragm, of the suction regulator shown in FIG. 2;

FIG. 6 is an enlarged top plan view of another of the components, i.e., a piston, of the suction regulator shown in FIG. 2;

FIG. 7 is a more enlarged isometric view of the piston shown in FIG. 6;

FIG. 8 is an enlarged sectional view taken along line 8-8 of FIG. 7;

FIG. 9 is an isometric view of another of the components, i.e., a spring, of the suction regulator shown in FIG. 2;

FIG. 10 is an enlarged isometric view of another of the components, i.e., a housing, of the suction regulator shown in FIG. 2;

FIG. 17 is an illustration of another exemplary system for automatically removing urine from a patient constructed in accordance with this invention wherein the system includes an adapter connecting the system to a conventional threaded male wall connector of a hospital suction line;

FIG. 18 is an enlarged front view of the adapter shown in FIG. 17;

FIG. 19 is an end view of the adapter taken along line 19-19 of FIG. 18;

FIG. 20 is a longitudinal sectional view of the adapter taken along line 20-20 of FIG. 19;

FIG. 21 is an enlarged isometric view of a valve member forming a portion of the adapter shown in FIGS. 18-20;

FIG. 22 is an end view of the valve member shown in FIG. 21;

FIG. 23 is an illustration of still another exemplary system for automatically removing urine from a patient constructed in accordance with this invention wherein the system includes an adapter and a splitter connecting the system to a conventional threaded male wall connector of a hospital suction line to enable the suction from the hospital's male wall connector to be used with some other apparatus while the system of the subject invention is connected to that wall connector;

FIG. 24 is an enlarged front view of the adapter and splitter shown in FIG. 23;

FIG. 25 is a side view of the adapter and splitter shown in FIG. 24;

FIG. 26 is an end view of the adapter and splitter taken along line 26-26 of FIG. 25;

FIG. 27 is a longitudinal sectional view of the adapter and splitter taken along line 27-27 of FIG. 26;

DETAILED DESCRIPTION OF THE PREFERRED EMBODIMENT

Figure 1:
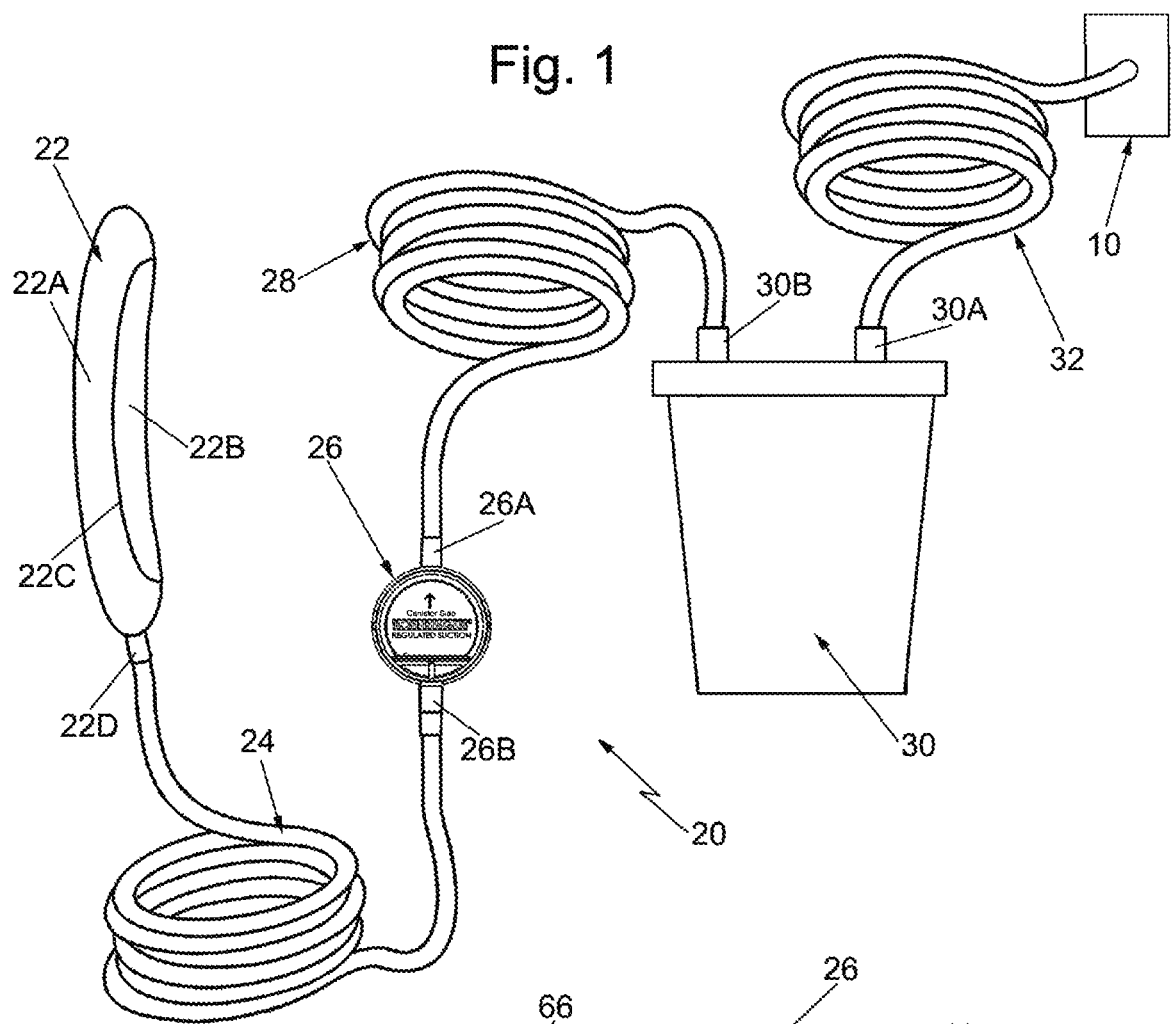
FIG. 1 is an illustration of one exemplary system for automatically removing urine from a patient constructed in accordance with this invention.

Referring now to the various figures of the drawing wherein like reference characters refer to like parts, there is shown in FIG. 1 one exemplary embodiment of a system 20 constructed in accordance with one exemplary preferred embodiment of this invention for automatically removing urine from a female patient. The system 20 may also be referred to as an external catheter urine collection system and the details of its construction and operation will be described later. Suffice it for now to state that the system 20 basically comprises a urine wicking member or device 22, a section 24 of conventional flexible suction tubing, a suction regulator 26, another section 28 of conventional flexible suction tubing, a urine collection suction receptacle or canister 30, and still another section 32 of conventional flexible suction tubing. The urine wicking device is preferably a female external catheter that can be constructed like any of the external catheters of the prior art described above. In the exemplary embodiment shown the device 22 is constructed like the PUREWICK® female external catheter.

The receptacle or canister 30 is of conventional construction and includes a port (to be described later) that is configured to be connected to suction source, e.g., a wall regulator 10 of the hospital's main suction line. The wall regulator 10 should be set to line vacuum or the maximum available vacuum pressure if a line function is not available. The canister 30 includes another port (also to be described later) which is connected to the proximal end of the tubing section 28. The distal end of the tubing section 28 is connected to one port, hereinafter identified as the "line suction port" 26A, of the suction regulator 26. The suction regulator 26 includes another port hereinafter identified as the "regulated suction port" 26B, which is connected to the proximal end of the tubing section 24. The distal end of the tubing section 24 is connected to the external catheter 22.

As will also be described later the suction regulator 26 is configured to enable fluid to flow through it from the external catheter to the canister nearing the maximum the hospital's suction line or regulator 10 is capable of sustaining without allowing the pressure to rise above a desired operating value, e.g., 40 mmHg, of the suction regulator 26 in the event the external catheter becomes sealed against the patient. With the preferred circuit of the system 20, i.e., with the suction regulator 26 located between the external catheter 22 and the urine collecting canister 30, the regulator 26 will be closer to the catheter 22 than if it was located between the canister 30 and the hospital suction line or regulator 10, thereby enabling the maximum possible urine flow, but necessitates the urine flowing through the regulator. To that end, the suction regulator 26 is intended to be a non-sterile, single-patient-use disposable unit having a fixed (e.g., factory-established) regulated set-point value to be described later.

The external catheter 22 basically comprises a soft, elongated hollow flexible member 22A in which a body of soft gauze 22B is located. The member 22A includes a longitudinally extending side window or opening 22C exposing the soft gauze body. The external catheter is designed to be disposed between the woman patient's separated gluteus and labia and in fluid communication with her urethral opening. A suction port 22D is located at one end of the member 22A and in fluid communication with the gauze body. The suction port is configured to be connected to the distal end of the tubing section 24, whereupon suction will be applied by that tubing section to the interior of the member 22A, whereupon any urine which the female patient had voided into the gauze body 22B will be pulled into the suction tubing 24 and carried by air from there to the suction regulator 26.

The suction receptacle or canister 30 is a conventional unit which serves to collect by suction urine automatically removed from the patient by the external catheter 22. To that end the receptacle or canister 30 is coupled to the hospital suction line or a wall mounted suction regulator 10 via the section of suction tubing 32. In particular, the canister or receptacle includes an inlet port 30A to which the distal end of the tubing section 32 is connected. In a typical application the length of the tubing section 32 is approximately 6 feet, with the inner diameter of the passageway through the tubing section 32 being approximately 0.25 inch. The canister also includes an outlet port 30B to which the proximal end of the tubing section 28 is connected. The line suction port 26A of the suction regulator 26 is connected to the distal end of the tubing section 28. In a typical application the length of the tubing section 28 is approximately 3 feet with the inner diameter of the passageway through the tubing section 28 being approximately 0.25 inch. The regulated suction port 26B of the suction regulator 26 is connected to the proximal end of the tubing section 24. The distal end of the tubing section 24 is connected to suction port 22D of the external catheter 22. In a typical application the length of the tubing section 24 is approximately 6 feet, with the inner diameter of the passageway through the tubing section 24 being approximately 0.25 inch.

With the system 20 as just described when suction is applied to the system 20 from the hospital's suction line or wall regulator 10, that high level of suction is conveyed through the canister and the associated tubing section 28 to the line suction port 26A of the suction regulator 26, whereupon it is regulated (e.g., reduced) by operation of the suction regulator to a much lower operating level, e.g., 40 mmHg. That reduced or regulated suction will appear on the suction port 26B of the regulator and from there through the associated tubing section 24 to the external catheter 22 to thereby draw urine from the external catheter back through the tubing section 24 into and through the regulator 26, and out through the tubing section 28 into the receptacle or canister 30 for collection therein. It should be noted that for many applications the operating level is preferably approximately 40 mmHg. However, that level could be raised up to approximately 80 mmHg, since some hospitals are comfortable with higher vacuum pressures. As will be appreciated by those skilled in the art the higher pressure makes the height of the receptacle or canister 30 relative to the patient less important.

If desired the system 20 may also include an overflow detector of any suitable construction to provide an indication that the amount of urine within receptacle has reached a predetermined threshold, e.g., is about to overflow, and/or to provide a signal to a controller (not shown) stop to halt the operation of the system so that no further urine is drawn into the receptacle until it can be emptied. For example, the canister 30 may include a shut off float valve and/or a filter at outlet 30A to prevent possible contamination of the hospital's main suction. Including a filter can create a pressure drop across the filter. In such circumstances it is advantageous to have the suction regulator 26 positioned upstream of the filter in order to maximize airflow rate while maintaining a low safe suction set-point.

The suction regulator 26 serves to ensure that a desired level of suction is applied to the external catheter to ensure proper and safe operation of the system, i.e., to maximize the rate at which urine may be withdrawn from the catheter into the receptacle or canister without subjecting the delicate tissue of the woman at her urethral opening to injury, e.g., a hematoma, from excess suction thereat.

Turning now to FIG. 3 the construction of the suction regulator 26 will now be described. To that end as can be seen the suction regulator basically comprises a label 34, a lid or cover 36, a flexible diaphragm 38, a piston 40, a sealing disk 42, a helical compression spring 44, and a housing body 46. The lid or cover 36 and the housing body 46 are configured to be connected together, as will be described later, to form a hollow housing assembly for housing the other components making up the regulator 26. The housing body 46 and the cover 36 are each formed of a rigid plastic, such as ABS.

As best seen in FIGS. 3, 10, 11 and 12, the housing body 46 includes a circular annular sidewall 48 projecting upward from a bottom wall 50. The circular sidewall extends about a central axis X of the suction regulator. A tubular extension 46A extends generally parallel to the undersurface of the bottom wall 50. The tubular extension 46A forms the heretofore identified line suction port 26A and includes a passageway 52 extending through it. The passageway 52 includes a linear section 52A extending radially from the axis X and whose outer or free end is open. Thus, that the distal end of the tubing section 28 can be connected to the tubular extension 46A whereupon the passageway extending through that tubing section will be in fluid communication with the linear passageway section 52A. The opposite end of the linear passageway section 52 terminates in an axially directed passageway section 52B centered about the axis X and terminates at the bottom wall 50. The upper end of the passageway section 52B is open at 52C, with the portion of the bottom wall 50 contiguous with the opening 52C forming a beveled or conical surface valve seat 54. The opening 52C is in fluid communication with a lower chamber 56 within the interior of the suction regulator 26. The lower chamber 56 will be described later. Suffice it for now to state that it is partially defined by the inner surface of the annular sidewall 48 and the diaphragm 38. Another tubular extension 46B projects radially outward from the annular sidewall 48. That tubular extension forms the heretofore identified line suction port 26B and includes a passageway 58 extending through it. The passageway 58 extends radially from the central axis X and parallel to the longitudinal axis of the passageway section 52A. The outer or free end of the passageway 58 is open. The inner end of the passageway 58 terminates at the sidewall 48 and is open and in fluid communication with the lower chamber 56 of the suction regulator. Thus, that the proximal end of the tubing section 24 can be connected to the tubular extension 46B, whereupon the passageway extending through that tubing section will be in fluid communication with the passageway 58 and the lower chamber 56.

The lid or cover 36 is a generally cup-shaped member having a top wall 60 and a circular annular sidewall 62. The sidewall includes a pair of diametrically opposed notches 64 immediately adjacent the lower edge of the sidewall. The notches are configured to receive respective diametrically opposed projecting tabs 66 of the housing body 46 to secure the lid or cover 36 to the housing body 46 and thus complete the housing assembly. The sidewall 62 of the lid or cover also includes an arcuate recess 68 (FIGS. 2 and 4) in the lower edge of the sidewall located midway between the notches 64. The recess 68 serves to receive the tubular extension 46B when the lid or cover is secured to the housing body.

The piston 40 is best seen in FIGS. 3, 6, 7 and 8 and basically comprises a unitary body formed of a rigid plastic, such as ABS. The body includes a central hub 70 whose top end terminates in a circular flange 72. The top surface of the flange is planar, but includes a circular recess 74 in the center thereof and extending into the hub 70. A plurality of ribs 76 extend outward radially from the hub and serve to reinforce the flange and center the spring 44 about the central axis X. The bottom surface of the hub 70 includes a recess 78 for receipt of the sealing disk 42. The disk 42 is fixedly secured in the recess 78 on the underside of the hub serves as a valve member to engage the valve seat 54 in the lower chamber 56 when excess suction is applied (as will be described later). The sealing disk 42 is formed of any suitable material, e.g., silicone rubber.

The diaphragm 38 is a rolling diaphragm formed of any resilient flexible material, e.g., Nitrile. The diaphragm includes a generally planar circular central portion 80 and a folded generally V-shaped or U-shaped edge portion 82 surrounding the central portion and terminating in a flanged generally planar thickened periphery 84. When fabricated the diaphragm is a molded component which is somewhat flat, but whose peripheral edge portion contiguous with the planar thickened periphery is everted (turned inside out) to assume the shape shown in FIGS. 3, 5, and 11 for use in the suction regulator 26. A small opening or hole 86 is located in the center of the central portion 80. The central portion 80 is disposed on the planar top surface of the piston 40, with the thickened periphery 84 of the diaphragm disposed on an annular ledge 88 at the upper end of the sidewall 48 of the housing body 46 between that ledge and the undersurface of the lid or cover 36. With the lid or cover secured to the housing base 46 the thickened periphery 84 of the diaphragm is tightly sandwiched between the ledge and the inner surface of the lid or cover. This arrangement divides the interior of the suction regulator into two chambers, the heretofore identified lower chamber 56 and an upper chamber 90. The upper chamber is formed between the inner surface of the cover or lid and the upper surface of the diaphragm. The lower chamber 56 is formed between the inner surface of the sidewall 48 of the housing body 46, and the undersurface of the portion of the diaphragm located adjacent its periphery and a portion of the undersurface of the piston.

Figure 2:
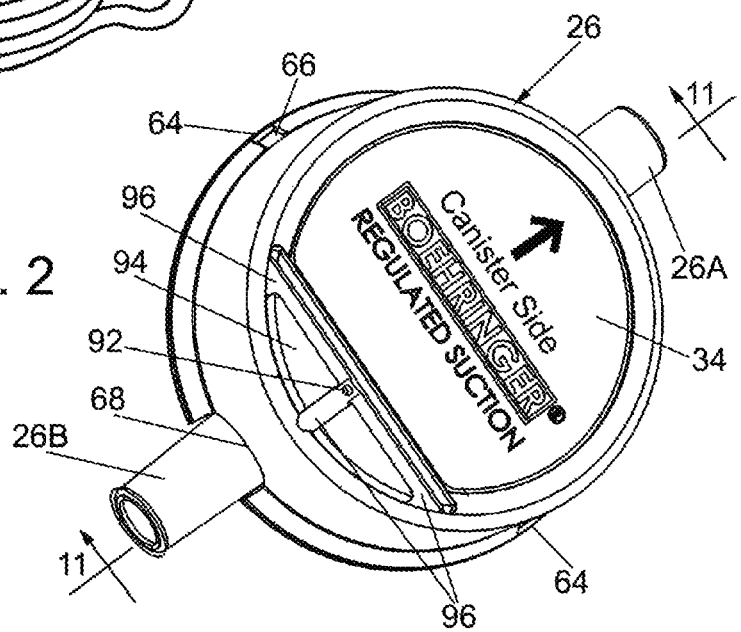
FIG. 2 is an enlarged isometric view of one of the components, i.e., a suction regulator, forming a portion of the system of FIG. 1.
Figure 11:
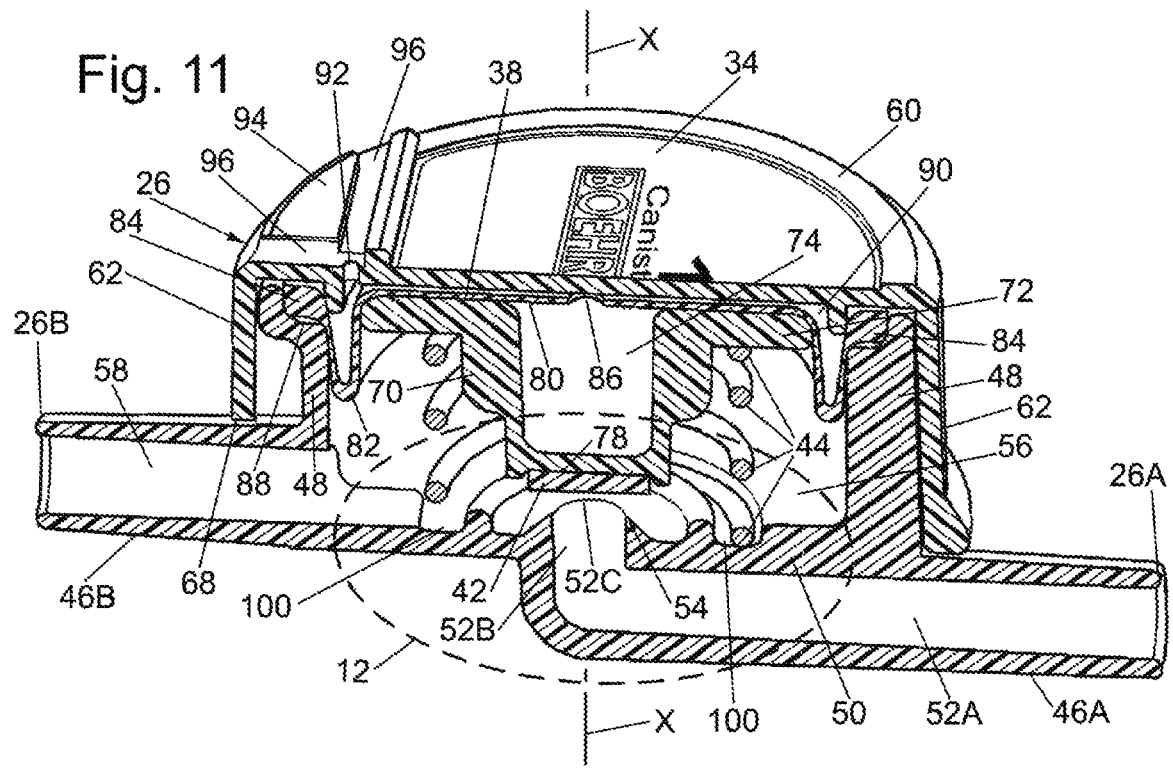
FIG. 11 is an enlarged sectional view taken along line 11-11 of FIG. 2.

The cover or lid includes a small opening or vent to the ambient atmosphere which will be referred to as the atmospheric reference port 92 (FIGS. 2 and 11). The atmospheric reference port ensures that the upper chamber 90 will be at the pressure of the ambient atmosphere. In particular, the port 92 extends through the thickness of the cover and is in fluid communication with the interior of upper chamber 90 to maintain that chamber at atmospheric pressure. Inasmuch as the atmospheric reference port 92 is located in the top surface of the cover, it is susceptible to being blocked or covered by a sticker, some other object or even the finger of a user. To prevent such an occurrence the lid or cover is shaped to prevent blockage of the port 92. In particular, the lid or cover includes a thickened portion 94 located adjacent the port 92 with an elongated shallow tripartite or T-shaped recess or slot 96 extending into the thickened portion. The outer or top end of the atmospheric reference port 92 is located at the bottom of the slot 96 at the intersection of the slot's various three sections and is in fluid communication with each of those sections. The outer end of each of the slot sections is open. Thus, if something should be on the top surface of the thickened portion 94 of the lid or cover disposed over the atmospheric reference port 92 air can still enter into that port via any open end of the T-shaped slot 96.

The label 34, which is configured to bear indicia or information regarding the suction regulator 26, e.g., the text and graphics like shown in FIGS. 2 and 3, is fixedly secured within a very shallow recess 98 (FIG. 4) in the top surface of the lid or cover adjacent the thickened portion 94 so its presence does not block the T-shaped slot 96.

Figure 12:
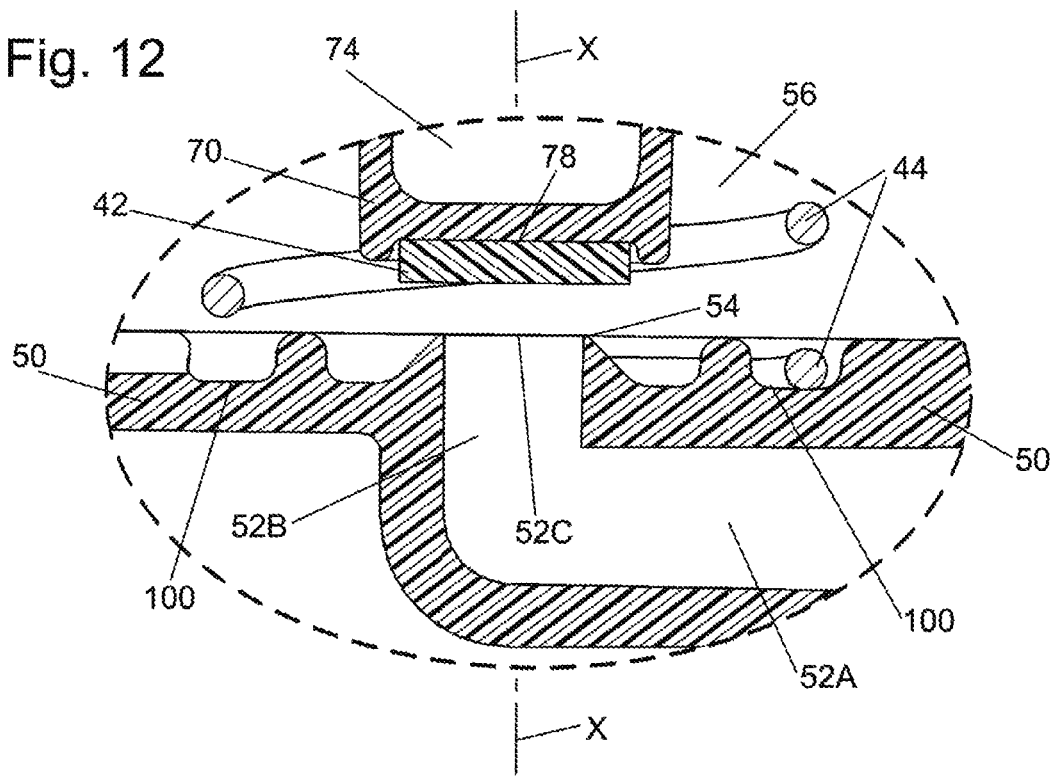
FIG. 12 is an enlarged sectional elevation view of the portion of the suction regulator shown within the broken oval designated by the reference number 12 in FIG. 11.

The spring 44 is a helical compression spring formed of any suitable material, e.g., stainless steel. As best seen in FIGS. 11 and 12, the spring is located within the lower chamber 56, with the upper end of the spring in engagement with the undersurface of the flanged portion 72 of the piston and surrounding a piston's central hub 70 and with the lower end of the spring located within an annular recess 100 in the bottom wall 50 of the housing body. The spring is under compression to bias the piston and diaphragm upward.

As mentioned above, the suction regulator 26 regulates the level of suction to a desired operating value, e.g., 40 mmHg, and provides the regulated suction to the external catheter (the urine wicking member) 22. To that end, the regulator 26 is configured to limit the amount of suction applied to the external catheter to that desired value even if a level of suction greater than that predetermined value is applied to the suction regulator from the suction source (particularly if the suction source is at a much higher level, which will typically be the case if the suction source is the hospital's suction line). The predetermined or desired suction value (hereinafter referred to has the "regulator's setpoint" or "regulated set-point value") is fixed and is factory-established by the spring 44 and the dimensions of the housing body 46, the cover or lid 36, the piston 40, the sealing disk 42, and the stiffness of the diaphragm 38. In this regard the pressure within the upper chamber 90 will be equal to atmospheric pressure by virtue of the communication of that chamber with the ambient atmosphere via the atmospheric reference port 92. With suction applied, the pressure within the lower chamber 56 will be lower than the atmospheric pressure within the upper chamber 90. The differential pressure between the chambers 90 and 56 will force the diaphragm 38 and the piston 40 downward toward the valve seat 54. The spring 44, however, will impart a counter force on the piston and diaphragm that opposes the differential pressure force forcing the piston downward such that the level of suction appearing at the regulated suction port 46B is the desired operating value, e.g., 40 mmHg.

If the suction applied via line suction port 26A is greater that the predetermined value or level the piston 40 and diaphragm 38 will move such that the sealing disk 42 on the bottom of the piston's hub 70 comes into engagement with the valve seat 54 thereby isolating the lower chamber 56 from the suction appearing on the line suction port 26A. This action thereby limits the level of suction in lower chamber and ultimately at external catheter 22 to the predetermined level (operating value). If, however, the suction applied via line suction port is less than the predetermined operating level the piston and diaphragm will only move part of the way downward. As such the level of suction applied to the line suction port 26A will equal that in the regulated suction port 26B and that applied to the external catheter 22.

It should be pointed out at this juncture that the suction regulator 26 is also configured to prevent the sealing disk 42 on the bottom of the piston from becoming stuck for an extended period of time on the valve seat 54 in the event of what will be referred to hereinafter as an "over-travel situation". In this regard, it has been determined that if the suction regulator 26 is operated in a manner such that a high level of suction is applied very rapidly, the piston may experience an over-travel wherein it moves downward very quickly such that the sealing disk 42 on the underside of the piston becomes stuck on the valve seat 54. Under this condition the suction tubing section 24 to the external catheter would have a higher level of vacuum (suction) than the regulator 26 was set to provide, e.g., 40 mmHg. The regulator could stay in that state for an extended/indefinite period of time, particularly if the external catheter becomes blocked, e.g., its wicking portion is in tight engagement with the vaginal tissue surrounding the urethral opening and not over the urethral opening itself. To prevent such an occurrence, the regulator 26 includes two "bleed holes". One bleed hole is the heretofore identified small hole 86 located in the center of the diaphragm 38. The second bleed hole 102 is located in the piston 40.

As best seen in FIGS. 3, 6, 7 and 8 the cylindrical cavity 74 in the piston contiguous with the planar top surface of the flanged portion 72 includes a radially extending recess. The bleed hole 102 is located in that recess and extends through the flanged portion of the piston to the underside of the flanged portion as best seen in FIG. 7. Since the bleed hole 86 in the diaphragm is located in the center thereof, i.e., on the central axis X, it will overlie and be in fluid communication with the cylindrical cavity 74 in the piston. The recess 104 is in fluid communication with the cylindrical cavity 74. Thus, the bleed hole 102 in the piston will be in fluid communication with the bleed hole 86 in the diaphragm.

Since the bleed hole 86 in the diaphragm is in communication with the upper chamber 90, that chamber will be in fluid communication with the lower chamber 56 via the communicating bleed holes 86 and 102. Hence, if the sealing disk 42 on the bottom of the piston should become stuck on the valve seat 54, air which enters into the upper chamber 90 via the atmospheric reference port 92 can then pass through the bleed hole 86 into the cylindrical cavity 74, and from there through recess 104 into the bleed hole 102, from whence it will enter into the lower chamber 56. The ingress of air into the lower chamber will decrease the vacuum within that chamber, thus enabling the spring 44 to move the piston 40 upward so that the sealing disk 42 is off of the valve seat 54.

In accordance with one exemplary preferred embodiment of the suction regulator 26, inner diameter of the lower chamber 56 is approximately 1.5 inch. The inner diameter of the upper chamber is approximately 1.5 inch. The spring is configured to naturally apply a bias force of approximately 1.0 pound. The inner diameter of the passageway 54 is approximately 0.25 inch. The inner diameter of the passageway 58 is approximately 0.25 inch. The opening 52C located within the bounds of the valve seat 54 is approximately 0.22 inch. The atmospheric reference port 92 is approximately 0.035 inch in diameter. The bleed hole 102 is approximately 0.016 inch in diameter. The bleed hole 86 is approximately 0.062 inch in diameter. Each tubing section 24, 28 and 30 is conventional having an internal passageway of approximately 0.25 inch in diameter, and each section is approximately six feet in length, but could be shorter or longer depending upon the application. In any case with a suction regulator sized as just described, in a system like that described during typical operation the flow rate of air into chamber 56 via bleed holes should be in the range of approximately 3 to 10 standard cubic feet per hour (SCFH). In fact, benchtop testing suggests that one version of the system 20 of this invention, making use of its disposable regulator 26 is capable of air flow rates up to 100 SCFH as compared to the 15 SCFH rate observed with some commercially available wall regulator set to the suggested 40 mmHg. As is known the conversion between SCFH is that a 1 SCFH flow is equivalent to 0.47 liters per minute (LMP) flow. The additional flow allows for increased urine capture at the interface of the actual catheter, faster drying of the catheter (which helps prevent skin breakdown and infection) and pulls the urine through the tubing into the canister 30 more efficiently. This is especially true if the tubing drapes down below the height of the patient and canister.

It must be pointed out at this juncture that the various components of the system shown and described above are merely exemplary of various components that may be used in accordance with this invention to provide the capabilities as discussed above. For example, the suction regulator 26 may be constructed somewhat similarly to the suction controller 300 shown in FIGS. 9A and 10A of pending U.S. application Ser. No. 14/227,587 entitled the Gastric Sizing Systems Including Instruments And Methods Of Bariatric Surgery filed on filed on Mar. 27, 2014, which is assigned to the same assignee as this invention and whose disclosure is specifically incorporated by reference herein. That suction controller if used in a system like the subject invention would be modified to omit the disk 314 and thus result in a cost saving. In the invention of that pending '587 application the disk 314 is provided to seal off the system when positive pressure is applied for leak testing. The system 20 of this invention and any other system constructed in accordance with this invention will never exceed atmospheric pressure, so a disk 314 is unnecessary. Moreover, the suction controller 300 of the pending '587 application if used in a system like that of this invention will need to be sized and configured to produce the desired regulated suction value, e.g., 40 mmHg.

Figure 13:
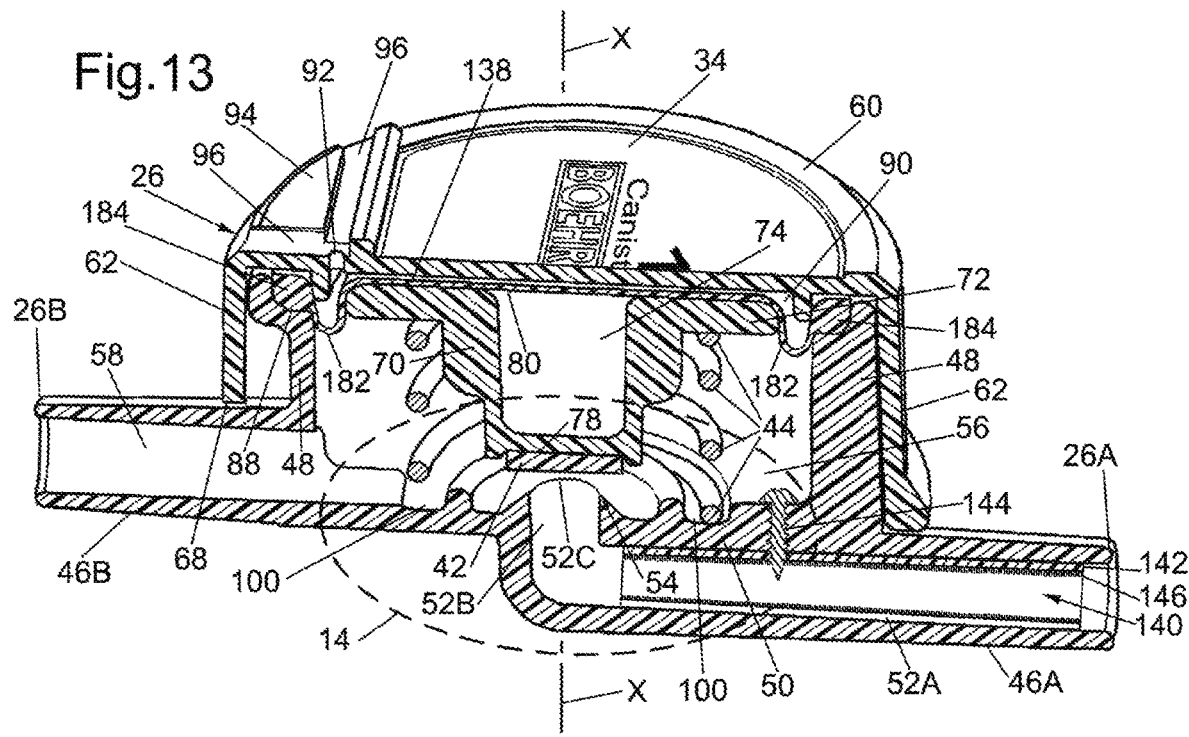
FIG. 13 is a sectional view, like that of FIG. 11, but showing another exemplary embodiment of a suction regulator constructed in accordance with this invention.
Figure 14:
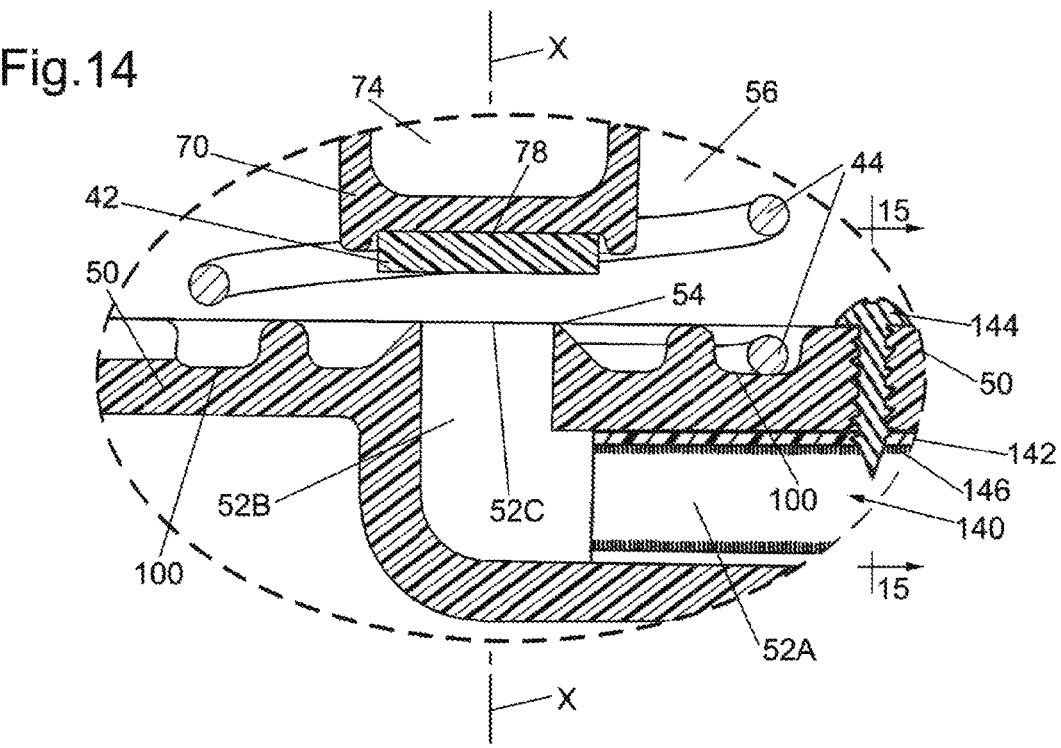
FIG. 14 is an enlarged sectional elevation view of the portion of the suction regulator shown within the broken oval designated by the reference number 14 in FIG. 13.
Figure 15:
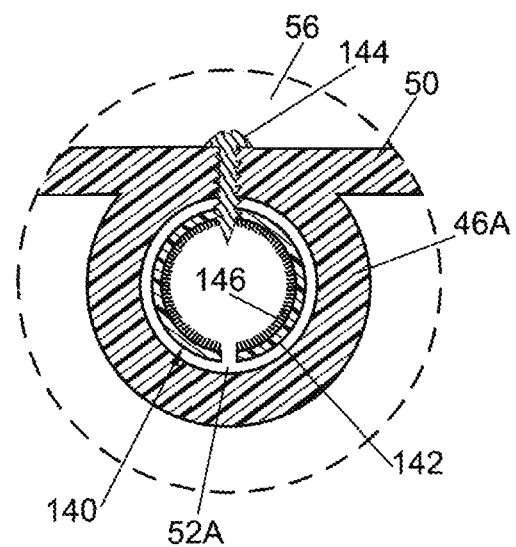
FIG. 15 is a sectional view taken along line 15-15 of FIG. 14.

In FIGS. 13-15 there is shown an alternative embodiment of a regulator 126 constructed in accordance with one preferred aspect of this invention. The regulator 126 is identical in virtually all respects to the regulator 26, except that the regulator 126 makes use of an alternative flexible diaphragm 138 and the addition of a noise suppression assembly 140. In the interest of brevity those components of the regulator 126 which are common with the regulator 26 will be given the same reference numbers and the details of the structure, arrangement and operation of those components will not be reiterated.

Figure 16:
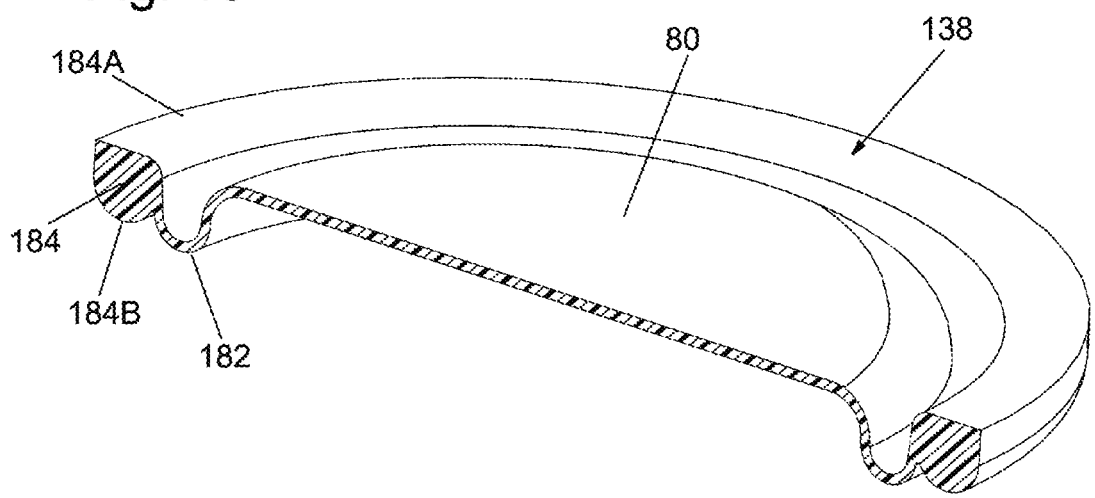
FIG. 16 is an enlarged isometric view, partially in section, of an alternative rolling diaphragm forming a portion of the suction regulator of FIGS. 13-15.
Figure 28:
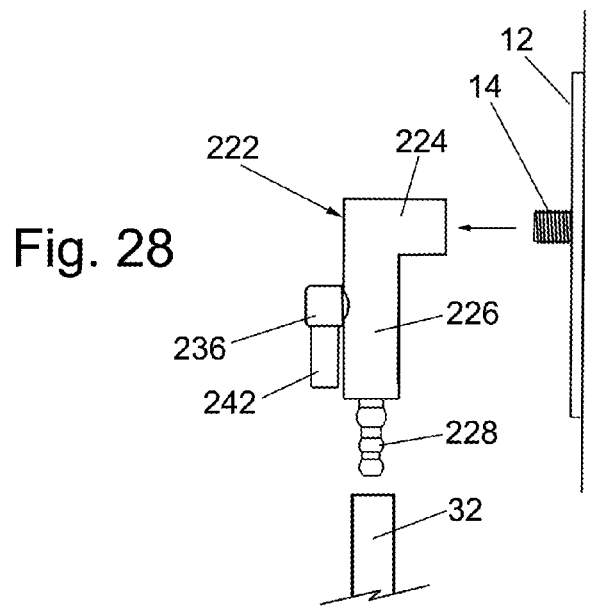
FIG. 28 is a side elevation view showing the adapter of FIGS. 18-20 being mounted on a conventional externally threaded connector of a port in the wall of a hospital or other care facility providing line suction.

The alternative diaphragm 138 is best seen in FIGS. 13 and 16, and like the diaphragm 38 is molded of a suitable material, e.g., silicone. However, unlike the diaphragm 38 it is molded into its ultimate shape and thus does not require any eversion of any portion of it to be in its final shape state. In particular, as can be seen in FIG. 16 the diaphragm 138 includes a generally planar circular central portion 80 and a short height generally U-shaped edge portion 182 surrounding the central portion and terminating in a flanged generally periphery 184. The periphery 184 includes a generally planar top surface 184A and an arcuate undersurface 184B. The undersurface is configured to rest on the annular ledge 88 of the housing. The U-shaped portion 182 is of a lower height than the portion 82 of the diaphragm 38. The diaphragm 138 operates in the same manner as the diaphragm 38 described above.

As should be appreciated by those skilled in the art, the fact that the diaphragm 138 is in its natural molded shape and does not require eversion of any portion of it renders the diaphragm less prone to "creep" over time. If the material making up the diaphragm were to "creep" due to the fact that a portion of the diaphragm was everted, it could result in some drifting or variation from the fixed set-point of the regulator. By eliminating the eversion of the diaphragm, the tendency of the diaphragm to creep over time is reduced, if not eliminated.

The diaphragm 138 does not include the heretofore identified bleed port 86 at the center of the central portion 80 (or at any other portion of the diaphragm 138 for that matter). The omission of a bleed port in the diaphragm has been determined to be acceptable for most applications, particularly if there is a substantial length of tubing 24 connected between the suction regulator and the external catheter. In this regard, it has been determined that even if the operation of the system results in the heretofore mentioned "overtravel" situation, the amount of suction applied to the patient would likely not reach an dangerously high level due to the substantial volume in the tubing 24 between the suction regulator and the external catheter and the volume of air within the external catheter. Moreover, there would likely be some leakage of air into that volume by virtue of movement of the patient breaking the seal around the catheter or by some leakage at the connection points of the tubing 24 to the catheter and to the suction regulator, whereupon the bias provided by the spring would ultimately result in the lifting of the sealing disk 42 off of the valve seat 54.

It has also been discovered that the regulator 26 may have a tendency to produce a whistling sound during operation caused by the flow of air fluid through it. In particular, the passageways 58 and 52A are offset from each other and interconnected by the perpendicularly oriented passageway portion 52B, thereby creating a tortuous flow path. Thus, the flow of air through that tortuous path, particularly if the air is flowing at a high rate of speed (which is the case of with the subject invention) results in the production of a high pitched whistling sound. Needless to say, that result is undesirable, particularly in a hospital setting. Accordingly, the regulator 128 includes the heretofore mentioned sound suppressor assembly 140. That assembly basically comprises a noise suppressor tube 142 and a screw 144 for mounting the tube. The tube 142 is formed from an elongated strip of a multi-hook fastener component, like that sold under the trademark VELCRO, which has been bent or curled into an elongated tube 142, with the hook-like projections 146 of the VELCRO strip extending generally radially inward. The tube 142 is located in the passageway 52A and fixedly secured in place by the screw 144. To that end, the screw 144 extends through the bottom wall 50 of the regulator, with the head of the screw being located within the chamber 56. With the tube 142 mounted as such the air flowing through the tube is disturbed by the inwardly directed hook-like projections, which action tends to suppress any noise that may have been created by that air flow.

Turning now to FIGS. 17-20 and 28 there is shown another exemplary preferred embodiment of the system 220 of this invention for automatically removing urine from a female patient. The system 220 basically comprises the external catheter urine collection system 20 described heretofore plus an adapter 222 for connecting the system 20 to a hospital's line suction port connector. In the interest of brevity the details of the construction, arrangement and operation of the various components making up the external catheter urine collection system 20 will not be reiterated. The adapter 222 is configured to mount connect the system 20 to the line suction port 12 of a hospital or some other facility providing suction to a patient, like shown in FIG. 28. As can be seen in that figure, the line suction port 12 includes a conventional externally threaded connector 14. The connector 14 has a passageway (not shown) through which suction from the hospital's line suction source is provided.

The adapter 222 includes a generally L-shaped body formed of any suitable material, e.g., Plated brass. The body of the adapter includes a base section 224 and an elongated section 226. The distal end of the elongated section 226 is in the form of a conventional bubble barb 228 for receipt of the proximal end of the tubing section 32. The elongated section 226 is of a generally circular profile when viewed from the distal end thereof. A generally L-shaped passageway is located in the body of the adapter 222. The L-shaped passageway includes a linear passageway section 230 extending through the bubble barb and through the elongated section centered on the central longitudinal axis of the elongated section. The proximal end of the passageway section 230 merges with and is in fluid communication with a passageway section 232. The passageway section 232 extends perpendicularly to the passageway section 230 and terminates in a larger diameter internally threaded bore 234. The internally threaded bore 234 serves as the inlet to the adapter 222 and is configured to receive the external threads of the hospital's wall connector 14 to mount the adapter 222 onto the line suction port 12. The internal diameter of the passageway section 232 preferably matches the internal diameter of the passageway extending through the line suction connector 14, e.g., 0.2 in. The internal diameter of the passageway section 230 is the same as the internal diameter of the passageway section 232.

The adapter 222 includes a valve 236 configured to be in either an open or closed position. When in the closed position (to be described shortly) the valve closes or blocks the passageway section 230 to isolate the passageway in the bubble barb 228 from the line suction provided at the connector 14, When the valve is open the passageway section 230 is unblocked so that the line suction provided at the connector 14 appears at the passageway in the bubble barb and hence is provided to the external catheter urine collection system 20. The valve 236 is best seen in FIGS. 21 and 22 and is a rotatable integral member, formed of any suitable material, e.g., Plated brass The valve basically comprises a cylindrical shaft 238, a hub 240 and a handle 242. The cylindrical shaft 238 is located within a correspondingly shaped cylindrical bore 244 (FIG. 20) intersecting the passageway section 230 perpendicularly thereto. A central axis Y extends through the bore 244 and serves as the rotation axis about which the shaft 238 of the valve rotates when the valve is moved from its closed state to its open state, and vice versa. The shaft 238 includes a hole 246 extending diametrically through it. The internal diameter of the hole 246 is the same as the internal diameter of the passageway section 230. The upper end of the shaft terminates in the hub 240, which is of slightly larger diameter than the diameter of the shaft. A generally planar handle 242 projects radially outward from the hub. The handle is configured to be rotated either clockwise or counterclockwise about the axis Y to either open the valve or close it. In particular, when the handle is rotated to the position wherein the hole 246 of the valve is axially aligned with the passageway 230 (e.g., the handle extending parallel to the elongated section 226), the valve will be in its open state so that suction is applied from the passageway section 232 to the passageway section 230 in the bubble barb 228. When the handle of the valve is rotated to the position wherein no portion of the hole 246 of the shaft is in communication with the passageway 230 (e.g., the handle extending perpendicular to the elongated section 226) suction appearing at the connector 14 will be isolated from the system 20.

Inasmuch as the adapter 222 when mounted on the connector 14 of the port 12 to connect the external catheter urine collection system 20 to the line suction at the port will take that port out of service for uses other than removing urine from the patient via the external catheter 22, this invention also contemplates use of another adapter enables the port 12 to be used with another suction device at the same time it is used with the system 20. To that end, FIG. 23 shows still another exemplary system 320 constructed in accordance with this invention for automatically removing urine from a patient and which includes an adapter/splitter 322 to enable some other suction-required device to access the line suction provided at the connector 14 of port 12 all the while the external catheter urine collection system 20 is connected to that connector by the adapter/splitter. The system 320 basically comprises the external catheter urine collection system 20 system 20 described heretofore plus the adapter/splitter unit 322. As in the case of the system 220, in the interest of brevity the details of the construction and operation of the various components making up the external catheter urine collection system 20 will not be reiterated.

Figure 29:
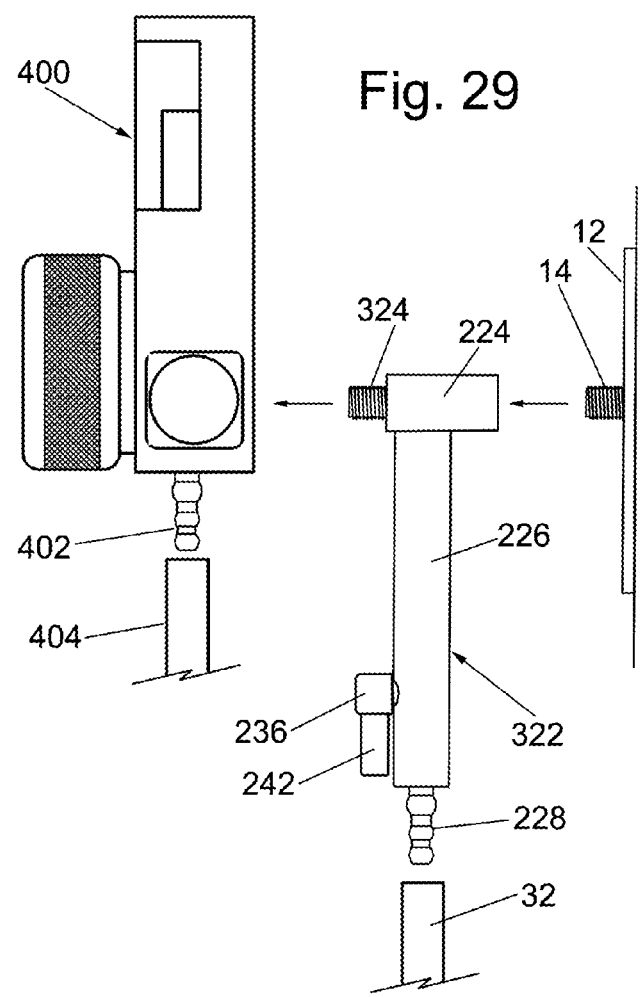
FIG. 29 is a side elevation view, similar to FIG. 28, but showing the adapter with splitter of FIGS. 24-27 being mounted on a conventional externally threaded connector of a port in the wall of a hospital or other care facility providing line suction and with a conventional suction regulator being mounted on the splitter.

As best seen in FIG. 29, the adapter/splitter 322 is configured to connect the external catheter urine collection system 20 to the threaded connector 14 of line suction port 12 of a hospital (or some other facility providing suction to a patient). The adapter/splitter 322 is in many ways identical in construction to the adapter 222, but also includes an externally threaded connector 324 having a passageway section 326 extending through it. The externally threaded connector 326 and its passageway section 326 together form the splitter portion of the adapter/splitter 322, thus providing another site at which the hospital's line suction is available. For example, as will be described shortly the externally threaded connector 324 can serve as the means for connecting and mounting a conventional suction regulator 400 thereon to control suction to some other device or equipment serving the patient.

Inasmuch as the splitter adapter 322 is very similar in construction to the adapter 222 in the interest of brevity the common components of the adapter 322 and the adapter/splitter 222 will be given the same reference numbers and the details of their structure, arrangement and operation will not be reiterated. Thus, as can be seen in FIGS. 24-26 the top of the base section 224 of the adapter/splitter 322 includes the heretofore identified externally threaded connector 324. As best seen in FIG. 27, the passageway section 326 is centered in the connector 324 and is coaxial and aligned with the passageway section 232 so that the sections 326 and 232 are in fluid communication with each other. As such passageway section 326 serves to bring suction from the line suction connector 14 to any device that may be connected to the externally threaded connector 324 irrespective of whether or not the valve 236 of the adapter/splitter 322 is open or closed. The internal diameter of the passageway section 326 is preferably the same as the internal diameter of the passageway sections 232 and 230.

Turning now to FIG. 29, the connector 324 of the adapter/splitter 322 is shown being connected to an internally threaded bore (not shown) of an exemplary suction regulator 400. The exemplary suction regulator 400 shown in FIG. 29 is a conventional suction regulator like that sold by Boehringer Laboratories, LLC, the assignee of the subject invention, under the model designation 3844. Other suction regulators available from the assignee of this invention as well as other manufacturers can be used by being connected to the threaded connector 324. Thus, while the system 320 is connected to the bubble barb 228 so that it can be used to withdraw urine from a patient via system 20, suction can be provided from the suction regulator 400 mounted on the connector 324 of the adapter/splitter 322 to provide suction for some other use. To that end, the suction regulator 400 includes a bubble barb 402 for disposition within an open proximal end of a tubing section 404, which will provide suction for some other application for the patient.

As should be appreciated from the discussion above the external catheter urine collection system of this invention and its method of use provides superior air flow through the external catheter. That feature is of considerable importance for transporting urine away from the patient. With prior art systems, if airflow is not adequate urine may spill out of the external catheter and the external catheter will remain damp against the patient's skin. By increasing the airflow through the catheter, as achieved by the suction regulator of the system of this invention, urine is more efficiently captured by the external catheter and leaks are reduced. Additionally, the improved air flow results in a drier external catheter helping to avoid skin maceration. Prior to the subject invention with a differential pressure of 55 mmHg applied to a typical flow circuit between the female external catheter and the collection canister of a prior art device a typical flow rate of 13 LPM (liters per minute) resulted. With the subject invention using three feet of ¼ inch tubing between the suction regulator of this invention and the external female catheter, a flow rate of 62 LPM was achieved with a differential pressure of 55 mmHg applied to the circuit. An adjustable hospital wall regulator like the Boehringer model 3844 identified above may provide free air flow rates of no more than: 18 LPM when set to 55 mmHg, 59 LPM when set to 120 mmHg, 64 LPM when set to 175 mmHg. The regulator of the subject invention provides a free airflow rate of approximately 100 LPM when factory calibrated to 55 mmHg differential pressure, approximately 101 LPM when calibrated to 120 mmHg differential pressure and approximately 102 LPM when calibrated to 175 mmHg differential pressure In fact, the subject invention enables an air flow rate of at least approximately 25 LPM with a differential pressure set to no more than 55 mmHg, an air flow rate of at least 35 LPM with a differential pressure set to no more than 100 mmHg, and a free flow rate of 60 LPM or more with higher differential pressures. Moreover, the system of this invention results in a ratio of the air flow rate (in LPM) squared to the pressure setting of the regulator (in mmHg) to be approximately at least 13. Those characteristics of the subject invention provide considerable advantages over the prior art.

Other advantages result from the external catheter urine collection system and its method of use. For example, since the suction regulator of this invention has a fixed regulated set-point value, users of the system do not have to pick and set a particular value for the suction to be applied to the patient's external catheter. As such a safe level of suction will be automatically be applied to the patient by the suction regulator without requiring hospital personnel or other operators to set the desired value of suction to be applied by the external catheter. Moreover, since the suction regulator has a fixed regulated set-point value, there is no need for it to include any dials or other indicators to provide the hospital personnel or other operators with a reading of the suction level being applied so that they could set the regulator to the desired set-point value. Accordingly, suction regulator constructed in accordance with this can be simple in construction, low in cost and easy to use. Also, since the suction regulator of the external catheter urine collection system of this invention provides controlled suction to the external catheter, the receptacle or container can be directly connected to the suction source, e.g., a hospital's wall line suction connector, without any other suction regulator to be interposed between that wall connector and the receptacle or canister, thereby reducing the need for additional capital purchases. Further still, since the suction regulator of this invention automatically applies a controlled level of suction to the patient the receptacle or canister can be located at any height with respect to the wall connector all the while ensuring that optimal drainage of urine into the receptacle or container is achieved. The use of a wall suction adapter, with or without a splitter, to connect the external catheter urine collection system to the line suction connector of the hospital or other care facility enables the external catheter urine collection system of this invention to be readily isolated from the hospital's suction line when desired. If the wall suction adapter includes a splitter like described above the hospital's line suction connector can be used to provide suction to some other device at the same time that it is providing suction to the external catheter urine collection system of this invention.

It must be pointed out at this juncture that various changes can be made to external catheter urine collection systems of this invention, in addition to changes in the suction regulators 26 and 126 and in the adapters 222 and 322. For example, while not preferred, it is contemplated that the suction regulator 26 could be located between the canister and the hospital suction source. However, such an arrangement will result in decreased urine flow due to the increased resistance of the longer flow path. Another alternative system contemplated by this invention entails integrating the suction regulator 26 (or a modification thereof) into the suction receptacle or canister 30. That alternative system would obviate the need for the suction tubing section 28 and decrease the number of components needed for the circuit, but may not make economic sense due to the commoditization of existing canisters. Still another alternative system of this invention contemplated entails designing an alternative external catheter or urine wicking device which has a regulator like that of the subject invention (or a modification thereof) built into it. That device should result in the absolute maximum urine flow possible, but would necessitate more frequent disposal of the regulator components (external catheters are changed multiple times per day), driving up the cost to users. Further still, some hospitals in which the subject system will be used have special regulator set-ups that allow for connection of a suction canister directly below the wall regulator. In such a case the tubing section 32 of the system 20 of this invention may be omitted. Also, it should be pointed out that the systems of this invention are not limited to use in hospitals, but can be used in any facility providing care to a female patient.

Without further elaboration the foregoing will so fully illustrate our invention that others may, by applying current or future knowledge, adopt the same for use under various conditions of service.

We claim:

1. A system for automatically removing by suction urine voided by a female comprising:
   an external catheter configured for external disposition in fluid communication with a urethra opening of the female, whereupon urine voided by the female is received by said external catheter;
   a receptacle or canister for collecting urine and configured to be coupled to a source of suction providing suction having a first value; and
   a suction regulator interposed between said external catheter and said receptacle or canister to regulate the amount of suction from said first value to a regulated value lower than said first value and to apply regulated suction at said regulated value to said external catheter, wherein urine from said external catheter is carried through said suction regulator and into said receptacle or canister by air and wherein said suction regulator comprises a body and a sound suppressor, said body having a first passageway configured to be coupled to the external catheter, a second passageway configured to be coupled to the source of suction, and third passageway connecting said first and second passageways to result in a tortuous fluid flow path through said passageways, said sound suppressor being located in said second passageway for reducing the sound of air flowing through said suction regulator.

2. The system of claim 1, wherein said second passageway is offset from said first passageway and interconnected thereto by a third passageway extending generally perpendicularly to said first and second passageways.

3. The system of claim 1, wherein said sound suppressor comprises a tube having a multitude of small hook-like projections extending generally radially inward.

4. The system of claim 2, wherein said sound suppressor comprises a tube having a multitude of small hook-like projections extending generally radially inward.

5. A system for automatically removing by suction urine voided by a female comprising:
   an external catheter configured for external disposition in fluid communication with a urethra opening of the female, whereupon urine voided by the female is received by said external catheter;

a receptacle or canister for collecting urine and configured to be coupled to a source of suction providing suction having a first value;

a suction regulator interposed between said external catheter and said receptacle or canister to regulate the amount of suction from said first value to a regulated value lower than said first value and to apply regulated suction at said regulated value to said external catheter, whereupon urine from said external catheter is carried through said suction regulator and into said receptacle or canister; and an adapter configured to be coupled between the source of suction and said receptacle or canister, said adapter comprising an inlet, a valve and a first connector, said inlet being configured to be connected to the source of suction, said first connector being configured to be connected to said receptacle or canister, said valve being configured to be in either a closed state or an open state, whereupon when in said closed state said receptacle or canister is isolated from said inlet, and when in said open state suction at said first value is provided from said inlet to said first connector and to receptacle or canister.

6. The system of claim 5, wherein said adapter includes an internal passageway having one end in communication with said inlet and another end in communication with said first connector, and wherein said valve includes a rotatable portion having an opening extending therethrough, said rotatable portion intersecting said internal passageway, whereupon when said rotatable portion is in a first rotatable position said rotatable portion blocks said internal passageway between said inlet and said first connector, and when said rotatable portion is in a second position said opening unblocks said internal passageway between said inlet and said first connector to enable suction at said first value to appear at said first connector.

7. The system of claim 5, wherein said first connector is configured to have a first section of suction tubing having a first end connected to it and a second end connected to said receptacle or canister.

8. The system of claim 7, wherein said first connector is a barbed bubble connector.

9. The system of claim 5, wherein said adapter additionally comprises a splitter including a second connector having a passageway section in fluid communication with said internal passageway between said inlet and said valve, whereupon suction at said first value is available from said inlet to said second connector irrespective of the state of said valve.

10. The system of claim 9, wherein said adapter includes an internal passageway having one end in communication with said inlet and another end in communication with said first connector, and wherein said valve includes a rotatable portion having an opening extending therethrough, said rotatable portion intersecting said internal passageway, whereupon when said rotatable portion is in a first rotatable position said rotatable portion blocks said internal passageway between said inlet and said first connector, and when said rotatable portion is in a second position said opening unblocks said internal passageway between said inlet and said first connector to enable suction at said first value to appear at said first connector.

* * * * *